(12) United States Patent
Hecht et al.

(10) Patent No.: US 7,786,065 B2
(45) Date of Patent: Aug. 31, 2010

(54) IONIC LIQUIDS DERIVED FROM PERACID ANIONS

(75) Inventors: Stacie Ellen Hecht, West Chester, OH (US); Gregory Scot Miracle, Hamilton, OH (US); Scott Leroy Cron, Fairfield, OH (US); Michael Stanford Showell, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 861 days.

(21) Appl. No.: 11/345,569

(22) Filed: Feb. 1, 2006

(65) Prior Publication Data

US 2006/0189499 A1 Aug. 24, 2006

Related U.S. Application Data

(60) Provisional application No. 60/654,722, filed on Feb. 18, 2005.

(51) Int. Cl.
C11D 1/62 (2006.01)
C11D 3/20 (2006.01)
C11D 3/39 (2006.01)
C11D 3/395 (2006.01)

(52) U.S. Cl. .................. 510/303; 510/235; 510/304; 510/328; 510/336; 510/337; 510/350; 510/372; 510/433; 510/504; 510/505; 134/42; 8/111

(58) Field of Classification Search .................. 510/235, 510/303, 304, 328, 336, 337, 350, 372, 433, 510/504, 505, 515; 8/137, 111; 134/42
See application file for complete search history.

(56) References Cited

U.S. PATENT DOCUMENTS

| | | | |
|---|---|---|---|
| 3,282,728 A | 11/1966 | Lacroux et al. | |
| 4,126,573 A | 11/1978 | Johnston et al. | |
| 4,189,311 A | 2/1980 | Laqua et al. | |
| 4,717,507 A | 1/1988 | Schwadtke et al. | |
| 5,705,466 A | 1/1998 | Baillely | |
| 5,731,101 A | 3/1998 | Sherif et al. | |
| 5,827,602 A | 10/1998 | Koch et al. | |
| 6,048,388 A | 4/2000 | Schwarz et al. | |
| 6,086,785 A | 7/2000 | Roesler et al. | |
| 6,277,808 B1 | 8/2001 | Tcheou et al. | |
| 6,288,281 B1 | 9/2001 | Nemeth et al. | |
| 6,339,182 B1 | 1/2002 | Munson et al. | |
| 6,372,829 B1 | 4/2002 | Lamanna et al. | |
| 6,472,360 B1 * | 10/2002 | Beggs et al. | 510/372 |
| 6,479,446 B1 | 11/2002 | Edward et al. | |
| 6,521,584 B1 | 2/2003 | Soldanski | |
| 6,521,585 B1 | 2/2003 | Yamashita et al. | |
| 6,767,882 B1 | 7/2004 | Jagannath et al. | |
| 6,808,557 B2 | 10/2004 | Holbrey et al. | |
| 6,824,599 B2 | 11/2004 | Swatloski | |
| 2001/0014654 A1 | 8/2001 | Davister et al. | |
| 2003/0109405 A1 * | 6/2003 | Kellar et al. | 510/375 |
| 2004/0005286 A1 | 1/2004 | Giroud | |
| 2004/0007693 A1 | 1/2004 | Moulton et al. | |
| 2004/0035293 A1 | 2/2004 | Davis, Jr. | |
| 2004/0054231 A1 | 3/2004 | Abbott et al. | |
| 2004/0077519 A1 | 4/2004 | Price | |
| 2004/0096932 A1 | 5/2004 | Kragl et al. | |
| 2004/0097755 A1 | 5/2004 | Abbott et al. | |
| 2004/0133058 A1 | 7/2004 | Arlt et al. | |
| 2004/0198902 A1 | 10/2004 | Yui et al. | |
| 2006/0090777 A1 | 5/2006 | Hecht et al. | |
| 2006/0094615 A1 | 5/2006 | Hecht et al. | |
| 2006/0094616 A1 | 5/2006 | Hecht et al. | |
| 2006/0094617 A1 | 5/2006 | Price et al. | |
| 2006/0094620 A1 | 5/2006 | Jordan, IV et al. | |
| 2006/0094621 A1 | 5/2006 | Jordan, IV et al. | |

FOREIGN PATENT DOCUMENTS

| | | |
|---|---|---|
| CN | 1081629 | 7/1999 |
| DE | 101 37 047 A1 | 2/2003 |
| EP | 0 723 006 A | 7/1996 |
| EP | 1 454 978 A | 9/2004 |
| FR | 1296756 | 5/1962 |
| FR | 2 101 710 A | 3/1972 |
| GB | 1 014 539 A | 12/1965 |
| JP | 3064368 | 3/1991 |
| JP | 5178798 | 7/1993 |
| JP | 06009767 A2 | 1/1994 |
| JP | 10265674 | 6/1998 |
| JP | 11084603 A2 | 3/1999 |
| JP | 2915208 B2 | 7/1999 |
| WO | WO 98/55581 A | 12/1998 |
| WO | WO 00/01793 A | 1/2000 |
| WO | WO 01/19200 A1 | 3/2001 |
| WO | WO 01/77486 A1 | 10/2001 |
| WO | WO 02/34722 A1 | 5/2002 |
| WO | WO 02/38784 | 5/2002 |
| WO | WO03/002702 * | 1/2003 |
| WO | WO 03/074494 A1 | 9/2003 |
| WO | WO 2004/022670 A1 | 3/2004 |
| WO | WO 2004/035018 A2 | 4/2004 |
| WO | WO 2004/067739 A2 | 8/2004 |

OTHER PUBLICATIONS

U.S. App. No. 11/263,391, filed Oct. 31, 2005, Price.

(Continued)

*Primary Examiner*—Gregory R Del Cotto
(74) *Attorney, Agent, or Firm*—Melissa G. Krasovec; Lenonard W. Lewis

(57) ABSTRACT

A novel class of ionic liquids and methods for their preparation are disclosed. Specifically, these novel ionic liquids can be derived from peracid anions. The present invention also relates to compositions containing these novel ionic liquids and method of using the same.

6 Claims, No Drawings

OTHER PUBLICATIONS

XP 002375958, 1993, Anufrieva, V, Chem. Abstract.
XP 002375959, 1991, Beilstein Institut zur Forderung, Chem. Abstract.
XP 002375959, 1991, Beilstein Institut zur Forderung, Chem. Abstract.
XP 002375960, 1989, J. Amer. Chem, Chem. Abstract.
XP 002375961, 1990, Beilstein Institut zur Forderung, Chem. Abstract.
XP 002375962, 1994, Beilstein Instut zur Forderung, Chem. Abstract.
XP 002375963, 1994, Beilstein Institut zur Forderung, Chem. Abstract.
John S Wilks, Air and Water Stable 1-Ethyl-3-methylimidazolium Based Ionic Liquids, The rank J. Seller Research Laboratory, United States Air Force Academy, Colorado, US, 1992, pp. 965-967.
J D Holbrey, Clean Products and Processes (1999) pp. 223, 236.
Richard Swatloski, Dissolution of Cellose with Ionic Liquids, Center for Green Manufacturing and Department of Chemistry, the University of Alabama, (2002) pp. 4974-4975 (Feb. 2002).
David Bradley, Super Solvents, Technology Ireland, Sep. 1999, pp. 47 & 48.
Brycki, Szafran, Formation of the Homoconjugated Cation (N-0 H O-N)+ of N-Dodecyl-N, N-Dimethylamine Oxide in Carbon Tetrachloride, Journal of Molecular Structure, 239 (1190) pp. 1-11, (1990).
Golding, J, Methanesulfonate and $p$-toluenesulfonate salts of the $N$-methyl-$N$-alkylpyrrolidinium and quaternary ammonium cations: novel low cost ionic liquids, Centre for Green Chemistry, School of Chemistry, Monash University, pp. 223-229, (Apr. 2002).
International Search Report, (Apr. 2006).

* cited by examiner

IONIC LIQUIDS DERIVED FROM PERACID ANIONS

CROSS-REFERENCE TO RELATED APPLICATIONS

This application claims the benefit of U.S. Provisional Application Ser. No. 60/654,722, filed on Feb. 18, 2005.

FIELD OF THE INVENTION

The present invention relates to a novel class of ionic liquids and methods for their preparation. Specifically, these novel ionic liquids can be derived from peracid anions. The present invention also relates to compositions containing these novel ionic liquids and method of using the same.

BACKGROUND OF THE INVENTION

Generally speaking, ionic liquids refer to a specific class of molten salts which are liquid at temperatures of 100° C. or below. Ionic liquids have very low vapor pressure and generate virtually no hazardous vapors. Due to the charged species comprising the ionic fluids, they provide a highly polar medium.

In recent years, there has been much interest in this class of novel materials. Ionic liquids have been extensively evaluated as environmental-friendly or "green" alternatives to conventional organic solvents for a broad range of organic synthetic applications. In addition, ionic liquids have also been used in organic synthesis applications as catalysts. Conventional ionic liquids for a wide range of chemical processes are described in "*Ionic Liquid*" by J. D. Holbrey and K. R. Seddon, and in *Clean Products and Processes*, Vol. 1, pp. 223-236 (1999). Other examples of ionic liquids are described in U.S. Pat. No. 6,048,388 and PCT publication no. WO 02/26701.

Furthermore, ionic liquids have also been found useful in chemical separation and extraction, as described, for example, in WO 02/074718.

Ionic liquids also have applications in electrochemistry, for example, in fuel cells, electrodeposition processes and other electrochemical applications.

Additionally, ionic liquids have been shown to be effective in applications where water-based chemistry can be problematic (for example, applications involving proton transfer or nucleophilicity), or in applications where certain coordination chemistry could have a damaging effect on the substrates involved.

Moreover, ionic liquids have found applications in consumer product formulations and industrial product formulations for surface treating, air treating, cleaning and other benefits, as described in WO 04/003120.

It is desirable to develop new classes of ionic liquids by converting certain conventional solid or semi-solid actives used in consumer or industrial product formulations into ionic liquids. Thus, the ionic liquids may be used as replacements of the traditional actives, such as surfactants, fabric softeners and bleaches. Moreover, the ionic nature and/or fluidity of these novel ionic liquids may provide additional advantages, such as ease of incorporating into the formulation, ability to incorporate higher concentration of the active functionalities into the formulations, lower viscosity of the resulting formulation, and/or improved soil removal capability of the resulting formulation.

It is also desirable to develop new classes of ionic liquids with additional advantageous properties. For example, new classes of water immiscible ionic liquids having bleach functionalities can be used in conventional aqueous based formulations to provide enhanced interactions with certain soils on the surface being treated and to extract or separate soils from the aqueous cleaning medium.

SUMMARY OF THE INVENTION

The present invention relates to an ionic compound comprising a cation and a peracid anion having the general Formula I below:

$$R^1\text{-G-OO}^\ominus \qquad \text{Formula I}$$

wherein G is an oxygen containing moiety selected from the group consisting of —C(O)—, —S(O)—, —S(O)$_2$—, —Se(O)—, —Se(O)$_2$, —OC(O)—, —OS(O), —OS(O)$_2$—, —OSe(O)—, —OSe(O)$_2$. —NHC(O)—, —NHS(O)—, —NHS(O)$_2$—, —NHSe(O)—, —NHSe(O)$_2$—, —NR$^2$C(O)—, —NR$_2$S(O)—, —NR$^2$S(O)$_2$—, —NR$^2$Se(O)—, or —NR$^2$Se(O)$_2$—; R$^1$ and R$^2$ are independently selected from the group consisting of C$_1$-C$_{16}$ linear or branched, unsubstituted or substituted alkyl, alkaryl, aralkyl and aryl moieties; the ionic compound has a melting temperature of about 100° C. or lower, or is flowable at a temperature of about 100° C. or lower.

Examples of suitable peracid anions include, but are not limited to, peracetic acid anion, pernonanoic acid anion, 6-(phthalimidoperoxy)hexanoic acid anion, and N-nonanoyl-6-aminoperoxycaproic acid anion. Such peracid anions, when paired with suitable cations such as those described herein could result in ionic compounds exhibiting liquid-like characteristics, such as melting or flowability at or below about 100° C.

DETAILED DESCRIPTION OF THE INVENTION

"Consumer product" as used herein refers to a material that is used by an end user (i.e., a consumer) in, on or around his/her person, house (such as kitchen surfaces, bathroom surfaces, carpets, floors, windows, mirrors and countertops), car (such as automobile interiors, automobile exteriorfabrics, dishes, cookware, utensils, tableware and glassware). "Consumer product composition" may also include the material used by institutional users (such as hotels, restaurants, offices) or by service providers (such as commercial dry cleaners and janitorial services).

"Industrial product" as used herein refers to a material that is used in a commercial process of making an article. Non-limiting examples include degreasing compositions for degreasing articles, such as metals, plastics and wood products; and textile treating compositions for processing and/or finishing textiles into fabric articles, such as garments, draperies and the like.

"Treating" as used herein refers to a composition or a process for cleaning, refreshing or maintaining the target surface or air. For example, "refreshing" includes the processes of imparting a pleasant odor to a fabric article, air, or a hard surface, or removing the wrinkled or worn appearance from a fabric article.

"Surface", "target surface" or "treated surface" as used herein refers to an inanimate, non-biological surface. Non-limiting examples of such surfaces are found in soft surfaces such as fabrics, fabric articles, textiles, fibers; and hard surfaces such as dishware, cookware, utensils, glassware, countertops, kitchen surfaces, bathroom surfaces, floors, windows, car interior and exterior, metals, and combinations thereof. These terms also include biological surfaces, such as hair, skin or teeth.

"Derived from" as used herein means ionic compounds are mixed or made from original materials; the ionic compounds may be in the form of mixtures of the original materials, or mixtures of reaction or decomposition products, or mixtures of all of the above.

"Hydrophilic ionic compound" or "water miscible ionic compound" as used herein refers to ionic compound that is partially or wholly miscible with water, i.e. it is capable of forming a visually homogenous or transparent mixture with water according to the Water Miscibility Test described herein.

"Hydrophobic ionic compounds" or "water immiscible ionic compounds" as used herein refers to ionic compounds that are relatively immiscible with water.

As used herein, "substituted" means that the organic compound or radical which:
  (a) is made unsaturated by the elimination of at least one element or radical; or
  (b) has at least one hydrogen in the compound or radical replaced with a moiety containing one or more carbon, oxygen, sulfur, nitrogen or halogen atoms; or
  (c) both (a) and (b).

Moieties which may replace hydrogen as described in (b) immediately above, that contain only carbon and hydrogen atoms, are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above carbon, oxygen, sulfur, nitrogen or halogen containing moieties can be substituted into each other in either a monovalent substitution or by loss of hydrogen in a polyvalent substitution to form another monovalent moiety that can replace hydrogen in the organic compound or radical.

It is also understood that the terms "ionic liquid", "ionic compound", and "IL" are used interchangeably herein.

The present invention relates to novel ionic liquids that are derived from compounds having peroxy moieties; when such peracid anions are used in detergent formulations for laundry, dish washing and hard surface cleaning, they exhibit bleaching functions. By reacting or mixing various peracid anions commonly used in detergent formulations with properly chosen counterions, these peracid anions can form ionic compounds having distinctive characteristics. For example, some peracid-derived ionic compounds are hydrophobic or water immiscible. In other examples, the peracid-derived ionic compounds are water miscible.

In some embodiments, the peracid-derived ionic compounds are liquids at temperatures of about 100° C. or below. That is, these ionic compounds exhibit a first order transition or a melting point at or below about 100° C., as measured by Differential Scanning Calorimetry (DSC). In other embodiments, the peracid-derived ionic compounds do not exhibit a melting point but are "flowable" at or below about 100° C. As used herein, the term "flowable" means the ionic compound exhibits a viscosity of less than about 10,000 cps at a temperature of about 100° C., preferably at a temperature range from about 20° C. to about 80° C. and more preferably from about 20° C. to about 60° C.

For certain applications, such as laundering, dish washing or hard surface cleaning, it is desirable to have ionic compounds that are liquids or "flowable" at temperatures ranging from about 20 to about 80° C., i.e., the typical operating temperatures for these applications.

Peracid-Derived Ionic Compounds

Non-limiting examples of peracid-derived ionic compounds of the present invention comprise a peracid anion having the general Formula I below:

   Formula I wherein G is an oxygen containing moiety selected from the group consisting of —C(O)—, —S(O)—, —S(O)$_2$—, —Se(O)—, —Se(O)$_2$, —OC(O)—, —OS(O)—, —OS(O)$_2$—, —OSe(O)—, —OSe(O)$_2$. —NHC(O)—, —NHS(O)—, —NHS(O)$_2$—, —NHSe(O)—, —NHSe(O)$_2$—, —NR$^2$C(O)—, —NR$^2$S(O)—, NR$^2$S(O)$_2$—, —NR$^2$Se(O)—, or —NR$^2$Se(O)$_2$—; wherein R$^1$ $^{and}$ $^{R2}$ are independently selected from the group consisting of C$_1$-C$_{16}$ linear or branched, unsubstituted or substituted alkyl, alkaryl, aralkyl and aryl moieties.

Exemplary embodiments of the ionic compounds of the present invention comprise peracid-derived anions including, but not limited to, peracetic acid anion, pernonanoic acid anion, 6-(phthalimidoperoxy)hexanoic acid anion, and N-nonanoyl-6-aminoperoxycaproic acid anion.

The peracid-derived anions described above may be paired with one or more of the following cations:
  (a) quaternary ammonium cations having the general formula:

wherein R$^1$ is C$_6$-C$_{24}$ alkyl, and R$^2$, R$^3$ and R$^4$ are C$_1$-C$_{20}$ alkyl or C$_1$-C$_{20}$ hydroxyalkyl; in some embodiments, R$^1$ is C$_{12}$-C$_{20}$ alkyl; in some embodiments, R$^2$, R$^3$ and R$^4$ may be C1-C6 alkyl or C1-C6 hydroxyl alkyl; in other embodiments, R$^1$ is a C$_6$-C$_{20}$ alkyl group and R$^2$, R$^3$ and R$^4$ are methyl or hydroxyethyl groups; non-limiting examples of commercially available quaternary ammonium cations suitable for use herein as the starting material for the ionic liquids include C$_{8-22}$ quaternary ammonium such as isostearyl ethyl imidonium ethosulfate available as Schercoquat IIS® from Scher Chemicals, Inc., quaternium-52 available as Dehyquart SP® from Cognis Corporation, and dicoco dimethyl ammonium chloride available as Arquad 2C-75® from Akzo Nobel Surface Chemistry LLC;
  (b) diester quaternary ammonium (DEQA) cations having the general formula:

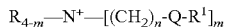

wherein m is 2 or 3; n is from 1 to 4; Q is —O—C(O)—, —C(O)—O—, —NR—C(O)—, or —C(O)—NR—; each R is hydrogen; C$_1$-C$_6$ alkyl or hydroxyalkyl, preferably methyl, ethyl, propyl, or hydroxyethyl, and more preferably methyl; poly($C_1$-$C_3$ alkoxy), preferably polyethoxy; benzyl; or a mixture thereof; each $R^1$ is independently unsubstituted or substituted $C_{11}$-$C_{21}$, preferably $C_{13}$-$C_{19}$, hydrocarbyl groups, such as linear or branched alkyl, alkenyl or alkoxyl groups; in one embodiment, the DEQA cation is an alkyl dimethyl hydroxyethyl quaternary ammonium as discussed in U.S. Pat. No. 6,004,922; in another embodiment, the DEQA cation has the general formula:

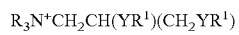

wherein each Y, R, $R^1$ have the same meanings as before; in yet another embodiment, the DEQA cation is [$CH_3$]$_3$$N^+$[$CH_2CH(CH_2O(O)CR^1)O(O)CR^1$] wherein each $R^1$ is in the range of $C_{15}$ to $C_{19}$;

(c) alkylene quaternary ammonium cations having the formula:

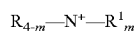

wherein m is 2 or 3; each R is independently an alkyl or hydroxyalkyl $C_1$-$C_6$ moiety, preferably methyl, ethyl, propyl or hydroxyethyl, and more preferably methyl; each $R^1$ is independently a linear or branched, substituted or unsubstituted, saturated or unsaturated $C_6$-$C_{22}$ alkyl or alkoxy moiety, preferably $C_{14}$-$C_{20}$ moiety, with the proviso that no more than one $R^1$ being less than about $C_{12}$ and one or more of the remaining $R^1$ being at least about $C_{16}$; in one embodiment, the cation is dialkylenedimethyl ammonium, such as dioleyldimethyl ammonium available from Witco Corporation under the tradename Adogen® 472; in another embodiment, the cation monoalkenyltrimethyl ammonium, such as monooleyltrimethyl ammonium, monocanolatrimethyl ammonium, and soyatrimethyl ammonium;

(d) difatty amido quaternary ammonium cations having the formula such as:

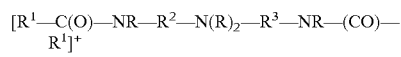

wherein each R is independently an alkyl or hydroxyalkyl $C_1$-$C_6$ moiety, preferably methyl, ethyl, propyl or hydroxyethyl, and more preferably methyl; each $R^1$ is independently a linear or branched, substituted or unsubstituted, saturated or unsaturated $C_6$-$C_{22}$ alkyl or alkoxy moiety, preferably $C_{14}$-$C_{20}$ moiety; $R^2$ and $R^3$ are $C_1$-$C_6$ alkylene moietites; non-limiting examples are commercially available from Witco under the Varisoft® tradename;

(e) $C_{8-22}$ quaternary surfactants such as isostearyl ethyl imidonium, available in its ethosulfate salt form as Schercoquat IIS® from Scher Chemicals, Inc., quaternium-52, available as Dehyquart SP® from Cognis Corporation, and dicoco dimethyl ammonium, available in its chloride salt form as Arquad 2C-75® from Akzo Nobel Surface Chemistry LLC;

(f) cationic ester surfactants such as discussed in U.S. Pat. No. 4,228,042, U.S. Pat. No. 4,239,660, U.S. Pat. No. 4,260,529 and U.S. Pat. No. 6,022,844;

(g) 4,5-dichloro-2-n-octyl-3-isothiazolone, which is available as Kathon® from Rohm and Haas;

(h) quaternary amino polyoxyalkylene derivatives, such as choline and choline derivatives;

(i) alkyl oxyalkylene cations;

(j) alkoxylate quaternary ammoniums (AQA) as discussed in U.S. Pat. No. 6,136,769;

(k) substituted and unsubstituted pyrrolidinium, imidazolium, benzimidazolium, pyrazolium, benzpyrazolium, thiazolium, benzthiazolium, oxazolium, benzoxazolium, isoxazolium, isothiazolium, imdazolidenium, guanidinium, indazolium, quinuclidinium, triazolium, isoquinuclidinium, piperidinium, morpholinium, pyridazinium, pyrazinium, triazinium, azepinium, diazepinium, pyridinium, piperidonium, pyrimidinium, thiophenium; phosphonium; in one embodiment, the cation is an substituted imidazolium cation having the formula:

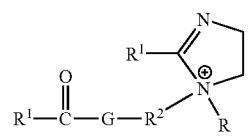

wherein each R and $R^1$ are as defined in cation (c) above; each $R^2$ is a $C_1$-$C_6$ alkylene group, preferably an ethylene group; and G is an oxygen atom or an —NR— group, $R^3$ is $C_1$-$C_{20}$ alkyl, $C_1$-$C_{20}$ alkoxy or $C_2$-$C_{20}$ alkenyl; for example, the cation 1-methyl-1-oleylamidoethyl-2-oleylimidazolinium is available commercially from the Witco Corporation under the trade name Varisoft® 3690; in another embodiment, the cation is alkylpyridinium cation having the formula:

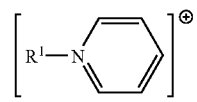

wherein $R^1$ is an acyclic aliphatic $C_8$-$C_{22}$ hydrocarbon group; in another embodiment, the cation is an alkanamide alkylene pyridinium cation having the formula:

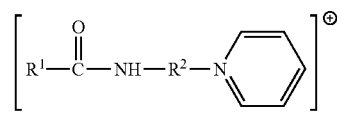

wherein $R^1$ is a linear or branched, saturated or unsaturated $C_6$-$C_{22}$ alkyl or alkoxy moiety, or a hydrocarbyl or substituted hydrocarbyl moiety, and $R^2$ is a $C_1$-$C_6$ alkylene moiety;

(l) cationic bleach activators having a quaternary ammonium moiety including but not limited to

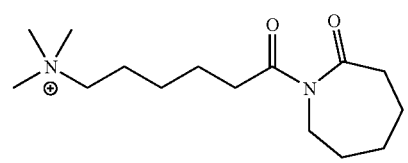

hexahydro-N,N,N-trimethyl-ζ,2-dioxo-1H-azepine-1-hexanaminium

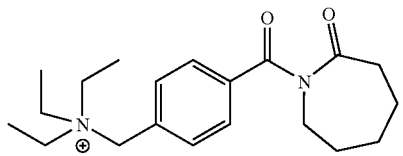

N,N,N-triethyl-4-[(hexahydro-2-oxo-1H-azepin-1-yl)carbonyl]benzenemethanaminium

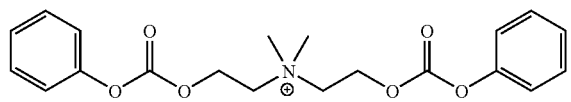

N,N-dimethyl-2-[(phenoxycarbonyl)oxy]-N-[2-[(phenoxycarbonyl)oxy]ethyl]ethanaminium

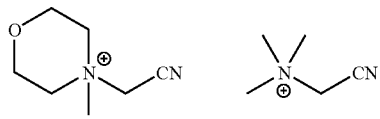

4-(cyanomethyl)-4-methylmorpholinium;
1-cyano-N,N,N-trimethylmethanaminium

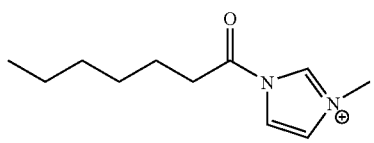

1-methyl-3-(1-oxoheptyl)-1H-Imidazolium these and other cationic bleach activators suitable for use herein as cations of the ionic liquids are disclosed in U.S. Pat. No. 5,599,781, U.S. Pat. No. 5,686,015, U.S. Pat. No. 5,686,015, WO 95/29160, U.S. Pat. No. 5,599,781, U.S. Pat. No. 5,534,179, EP 1 253 190 A1, U.S. Pat. No. 6,183,665, U.S. Pat. No. 5,106,528, U.S. Pat. No. 5,281,361, and Bulletin de la Societe Chimique de France (1973), (3)(Pt. 2), 1021-7;

(m) cationic anti-microbial agents, such as cetyl pyridinium, chlorhexidine and domiphen;

(n) alkylated caffeine cations, such as

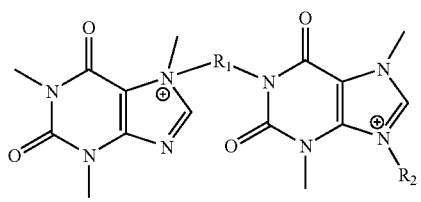

wherein $R_1$ and $R_2$ are $C_1$ to $C_{12}$ alkyl or alkylene groups;

(o) alkyl poly amino carboxylates, such as

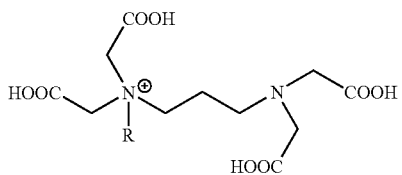

wherein R=$C_8$ to $C_{22}$ or is coco, tallow or oleyl; non-liminting examples include Ampholak® 7CX/C, Ampholak® 7TX/C, and Ampholak® XO7/C from Akzo Nobel; and (p) mixtures thereof.

The wide selection of cations provides the advantage of customizing the ionic liquids of the present invention for specific application or desired benefit. These anions can be selected and mixed with the surfactant derived cations described herein such that properties of the resulting ionic liquids can be customized. For example, water immiscible ionic liquids can be particularly useful in removing certain soils from the surface being treated and in extracting/separating soils from the aqueous medium.

In some embodiments, water immiscible ionic liquids comprise cations having the formula:

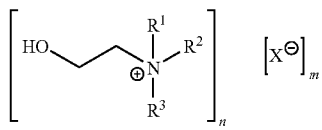

wherein $R^1$—$R^3$ are selected from the group consisting of linear or branched, substituted or unsubstituted, alkyl, aryl, alkoxyalkyl, alkylenearyl hydroxyalkyl, or haloalkyl, and mixtures thereof; X is a peracid-derived anion such as those described hereinabove; m and n are chosen to provide electronic neutrality; further wherein the ionic liquids are water immiscible when at least one of $R^1$—$R^3$ is $C_{12}$ or higher; or at least two of $R^1$—$R^3$ are $C_{10}$ or higher; or all three of $R^1$—$R^3$ are $C_6$ or higher; and X is a peracid-derived anion containing at least a $C_8$-$C_{22}$ alkyl group.

In some embodiments, the water immiscible ionic liquids comprise a cation selected from the group consisting of trimethyloctyl ammonium cation, triisooctylmethyl ammonium cation, tetrahexyl ammonium cation, tetraoctyl ammonium cation, and mixtures thereof.

Ionic Liquids Applications

The ionic liquids of the present invention may be used in various consumer, institutional or industrial products, including but not limited to a laundry detergent, a dish cleaning detergent, a hard surface cleaning composition, a dry cleaning composition, an air care composition, a car care composition, a textile treating composition, or an industrial degreasing composition.

Without wishing to be bound by theory, it is believed that the fundamental chemical and/or physical properties on ionic liquids can be used advantageously in the surface or air treating compositions. In one aspect, ionic liquids have a high solubilizing ability, due to their high polarity and charge density; thus, ionic liquids can be an effective solvent for soils. Therefore, composition containing ionic liquids exhibit enhanced soil removal ability, compared to similar compositions without the ionic liquids. In another aspect, the functional groups and counterions of the ionic liquids can be varied such that the resulting ionic liquids are "tuned" to the characteristics of the target soil or surface. For example, the functional groups can be selected such that the resulting ionic liquids have the desired degree of hydrophilicity or hydrophobicity to interact more strongly or preferentially with the target soil or surface. The mechanisms by which ionic liquids can effectively interact with soil or substrates include, but are not limited to, charge transfer, ion exchange, van der Waals forces, and hydrogen bonding. In yet another aspect, the effective solvating property of the ionic liquids enables them to dissolve certain polymeric materials, which are soluble in few if any solvent media. Examples of such hard-to-dissolve polymers include, but are not limited to, biofilms, baked-on or cooked-on soils, polymerized soils, and the like.

In fabric cleaning and/or treating applications, ionic liquids provide high polarity without the detrimental effects of water. For example, water can causes damages to certain fabrics; the damages include, but are not limited to, shrinkage, dye loss, shape loss, and wrinkles.

Additionally, the nucleophilic and protic nature of water can lead to undesirable effects when formulating compositions intended for treating fabrics or similar soft surfaces. For example, water's ability to swell and/or form hydrogen bond with cellulose can lead to increased abrasion and shrinkage of cellulosic fabrics. Ionic liquids can be tailored or selected to be non-nucleophilic and/or aprotic such that they would not have these adverse effects on cellulosic fibers or fabrics.

In still another aspect, the ionic liquids are non-volatile and nonflammable, and have high thermal stability; as such, they are especially suitable for use in surface or air treating compositions for both safety and aesthetic reasons. It is often undesirable to have chemical vapors or low flash point compounds associated with compositions used in a consumer, industrial or institutional setting. It is also undesirable to have compositions that will leave unsightly streaks on surfaces treated by them. Commonly used organic cleaning solvents tend to have chemical vapors that may be toxic, flammable, or malodorous. Other commonly used compositions may leave unsightly or streaky residue on the treated surfaces, thus, they need to be removed (e.g., by wiping, rinsing, and the like) from the surfaces after application. In contrast, ionic liquids have essentially no vapor pressure (i.e., no detectable vapor pressure at or near room temperature); compositions using ionic liquids as the active ingredients or the solvents may reduce or eliminate the problems associated with chemical vapors, thus, are highly advantageous. Additionally, such compositions can be used as a leave-on product and produce aesthetically pleasing results on the treated surfaces.

Thus, the unique and customizable physical and chemical properties allow ionic liquids to overcome several problems that persist in prior art compositions used in treating soft or hard surfaces or air.

Accordingly, the present invention also relates to compositions, consumer products, and industrial products comprising the peracid-derived ionic liquids, and the methods of using the same in following applications: dish/food cleaning, home care (kitchen/bath), biofilm removal, dry-cleaning (home and commercial), laundry (pretreatment, cleaning, and fabric care), textile processing and finishing, car care (interior and exterior), industrial degreasing, and air care.

The ionic liquid may be used in these applications or products as a pure solvent (i.e. as a pure, undiluted ionic liquid or ionic liquid composite); as a co-solvent in conjunction with water or other organic solvents; or as an active where the continuous phase is water or another solvent (e.g. linear or cyclic siloxanes, halocarbons). Various adjunct ingredients known in the art may be incorporated into such compositions. In certain embodiments, water and/or solvent may be present in the composition at least about 0.01% or at least about 1% or at least about 10%, and less than about 50% or less than about 30% or less than about 20% by weight of the composition.

The ionic liquid compositions may be formulated in the form of liquid, gel, paste, foam, or solid. When the composition is in the solid form, it can be further processed into granules, powders, tablets, or bars.

The ionic liquid compositions may also comprise adjunct ingredients commonly used in air or surface treating compositions. When present, an adjunct ingredient may comprise from about 0.01 to about 10%, preferably from about 0.1 to about 5% by weight of the composition.

Suitable adjunct ingredients may be selected from the group consisting of enzymes, bleaches, surfactants, perfumes, co-solvents, cleaning agents, antibacterial agents, antistatic agents, brighteners, dye fixatives, dye abrasion inhibitors, anti-crocking agents, fabric softeners, wrinkle reduction agents, wrinkle resistance agents, soil release polymers, sunscreen agents, anti-fade agents, builders, sudsing agents, composition malodor control agents, dyes, colorants, speckles, pH buffers, waterproofing agents, soil repellency agents, and mixtures thereof.

Examples of suitable adjunct ingredients are disclosed in U.S. Pat. No. 6,488,943, Beerse et al.; U.S. Pat. No. 6,514,932, Hubesch et al.; U.S. Pat. No. 6,548,470, Buzzaccarini et al.; U.S. Pat. No. 6,482,793, Gordon et al.; U.S. Pat. No. 5,545,350, Baker et al.; U.S. Pat. No. 6,083,899, Baker et al.; U.S. Pat. No. 6,156,722, Panandiker et al.; U.S. Pat. No. 6,573,234, Sivik et al.; U.S. Pat. No. 6,525,012, Price et al.; U.S. Pat. No. 6,551,986, Littig et al.; U.S. Pat. No. 6,566,323, Littig et al.; U.S. Pat. No. 6,090,767, Jackson et al.; and/or U.S. Pat. No. 6,420,326, Maile et al.

In some embodiments, such as laundry or dishwashing, ionic liquid compositions may be applied to the fabric or dish directly, or may be diluted with water to form a wash liquor, which contacts the fabric or dish. In other embodiments, the ionic liquid compositions may be in the form of a liquid, which can be applied to the target surface as a liquid spray, as an aerosol spray, or as a pour-on liquid, which can be poured onto the target surface directly or indirectly via a substrate such as a fibrous web substrate (made by woven, nonwoven or knitted technologies), a pulp-based substrate (made by airfelt or wet-laid technologies, including paper towels and tissues), a sponge, or a foam substrate. Another mode of use would be to incorporate ionic liquid compositions into or onto these substrates (e.g. impregnated in a wipe or a mitten), which would alleviate residue problems in those applications where complete dry down is needed.

Determination of Presence of Available Oxygen (AvO) in Peracid Ionic Liquid

A solution of the peracid ionic liquid (25 mg in 1 ml methanol) is added to a solution of acetic acid (2 ml) and potassium iodide (1 ml, 10 wt % aqueous solution). Visual observation of a yellow color against a white background (for example, a sheet of white paper) within 10 seconds of addition is a positive result for AvO. No color generation within 10 seconds of addition is a negative result for AvO.

Characterization of the Ionic Liquids

The structures of the ionic liquids of the present invention are characterized by NMR (nuclear magnetic resonance). The melting temperatures of the ionic liquids are characterized by DSC (differential scanning calorimetry) at a scan rate of 10 degrees C. per minute on heating cycles and 5 degrees per minute on cooling cycles.

EXAMPLE 1

Preparation of tetraoctyl amine pernonanoic acid

Pernonanoic acid (3 g of 90% concentration, 15.4 mmoles) is dissolved in 50 ml HPLC grade methanol (containing 100 ppm diethylenetriamine penta(methylphophonic acid)) at room temperature. To this mixture, sodium hydroxide (2.5 g of 25 wt % aqueous solution, 15.4 mmoles) and di-(tetraoctylammonium) sulfate (39.5 g of 20 wt % in methanol, 7.9 mmoles) are added. Resultant solution is stirred 5 minutes at room temperature followed by concentrating (i.e., removing solvent) on rotary evaporator at 30 degrees C. for 20 minutes. The resultant mixture is stirred at room temperature for 30 minutes at 1 mm Hg to yield 4.5 g of product, which appears as a viscous oil. The product tested positive for AvO.

EXAMPLE 2

Preparation of dimethyl hydroxyethyl dodecyl amine 6-(phthalimidoperoxy)hexanoic acid The starting material, 6-(phthalimidoperoxy)hexanoic acid (3 g of 70% concentration, 7.6 mmoles) is dissolved in 50 ml HPLC grade methanol (containing 100 ppm diethylenetriamine penta(methylphophonic acid)) at room temperature. To this mixture, sodium hydroxide (1.2 g of a 25 wt % aqueous solution, 7.6 mmoles) and di-(dimethyl hydroxyethyl dodecylammonium) sulfate (9.33 g of 25 wt % in methanol, 3.8 mmoles) are added. Resultant solution is stirred for 5 minutes at room temperature, followed by concentrating (i.e., removing solvent) on rotary evaporator at 30 degrees C. for 20 minutes. The resultant mixture is stirred at room temperature for 30 minutes at 1 mm Hg to yield 4.5 g of product, which appears as a viscous oil. The product tested positive for AvO.

The following are non-limiting examples of consumer product compositions containing ionic liquids of the present invention.

| | Composition Examples | | | | | |
|---|---|---|---|---|---|---|
| | 3 | 4 | 5 | 6 | 7 | 8 |
| Tetraoctyl amine pernonanoic acid | — | 5 | 30 | 2 | — | 10 |
| Dimethyl hydroxyethyl dodecyl amine 6-(phthalimidoperoxy)hexanoic acid | 10 | — | 5 | — | 60 | 10 |
| Aesthetic Agents[1] | 1 | 1 | 1 | 1 | 1 | 1 |
| Enzymes[2] | 2 | — | — | 1 | — | — |
| Adjuncts[3] | 40 | 30 | 10 | 25 | 5 | 5 |
| Co-solvent[4] | — | 5 | 2 | — | 15 | 2 |
| Water | balance | balance | balance | balance | balance | balance |

[1] aesthetic agents may be selected from the group consisting of dyes, colorants, speckles, perfumes and mixtures thereof;
[2] enzymes may be selected from the group consisting of proteases, amylases, lipases, and mixtures thereof;
[3] adjuncts may be selected from the group consisting of surfactants, enzymes, fabric softeners, non-oxygen containing bleaching agents, preservatives, pH buffers, and mixtures thereof;
[4] co-solvents may be selected from the group consisting of ethanol, isopropanol, propylene glycol, and mixtures thereof.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An ionic liquid in the form of a liquid consisting of a cation and a peracid anion having the general formula:

$$R^1\text{—}G\text{—}OO^\ominus$$

wherein G is —C(O)— and $R^1$ is selected from the group consisting of $C_1$-$C_{16}$ linear or branched, unsubstituted or substituted alkyl, alkaryl, aralkyl, and aryl moieties, wherein said ionic liquid has a melting temperature of about 100° C. or lower; or is flowable at a temperature of about 100° C. or lower and the cation is diester quaternary ammonium (DEQA) cation having the formula:

$$R_{4-m}\text{—}N^+\text{—}[(CH_2)_n\text{-}Q\text{-}R^1]_m$$

wherein m is 2 or 3; n is from 1 to about 4; Q is —P—C(O)—, —C(O)—O—, —NR—C(O)—, or —C(O)—NR—; each R is independently selected from hydrogen; $C_1$-$C_6$ alkyl or hydroxyalkyl; poly($C_1$-$C_3$ alkoxy); benzyl; or a mixture thereof; each $R^1$ is independently selected from unsubstituted or substituted $C_{11}$-$C_{21}$ hydrocarbyl groups.

2. A method for treating a target surface comprising the step of:
contacting a target surface with said ionic liquid of claim 1.

3. The method according to claim 2 wherein the target surface is selected from the group consisting of soft surfaces, hard surfaces, and combinations thereof.

4. The method according to claim 3 wherein the soft surfaces are selected from the group consisting of fabric articles, textiles, fibers, and combinations thereof; and the hard surfaces are selected from the group consisting of dishware, cookware, utensils, glassware, countertops, bathroom surfaces, kitchen surfaces, floors, windows, car interiors, car exteriors, metal and mixtures thereof.

5. An article of manufacture comprising a substrate and said ionic liquid according to claim 1 associated with the substrate.

6. The article according to claim 5 wherein the substrate is selected from the group consisting of a woven fibrous substrate, a non-woven fibrous substrate, a knitted fibrous substrate, a pulp-based air-felt substrate, a pulp-based wet-laid substrate, a foam, a sponge, and combinations thereof.

* * * * *